United States Patent [19]
Brophy et al.

[11] Patent Number: 4,652,688
[45] Date of Patent: Mar. 24, 1987

[54] PROCESS FOR THE PRODUCTION OF HYDROCARBONS FROM HETERO-SUBSTITUTED METHANES

[75] Inventors: John H. Brophy, Camberley; Josephus J. H. M. Font Freide, Weybridge; Jeremy D. Tomkinson, Staines, all of England

[73] Assignee: The British Petroleum Company, p.l.c., London, England

[21] Appl. No.: 809,887

[22] PCT Filed: Apr. 24, 1985

[86] PCT No.: PCT/GB85/00175
§ 371 Date: Dec. 10, 1985
§ 102(e) Date: Dec. 10, 1985

[87] PCT Pub. No.: WO85/04863
PCT Pub. Date: Nov. 7, 1985

[30] Foreign Application Priority Data
Apr. 24, 1984 [GB] United Kingdom ............... 8410479

[51] Int. Cl.$^4$ .............................................. C07C 1/26
[52] U.S. Cl. ..................................... 585/408; 585/469; 585/641; 585/642; 585/733; 585/935; 585/943; 585/310
[58] Field of Search ............... 585/408, 469, 641, 642, 585/733, 943, 935, 310

[56] References Cited

U.S. PATENT DOCUMENTS

| 2,320,274 | 5/1943 | Gorin | 585/469 |
| 3,702,886 | 11/1972 | Arguer et al. | 502/71 |
| 3,894,107 | 7/1975 | Butter et al. | 585/640 |
| 4,043,825 | 9/1977 | Owen et al. | 585/943 |
| 4,071,573 | 1/1978 | Owen et al. | 585/469 |

FOREIGN PATENT DOCUMENTS 8300483  2/1983  European Pat. Off. ............ 585/640

OTHER PUBLICATIONS

Chemical Abstract 93:204045y (1980).

Primary Examiner—Asok Pal
Attorney, Agent, or Firm—Brooks Haidt Haffner & Delahunty

[57] ABSTRACT

A monohalomethane is converted to a product comprising hydrocarbons having at least 2 carbon atoms and in particular aliphatic hydrocarbons in the gasoline boiling range by contact with a synthetic crystalline gallosilicate zeolite loaded either with at least one modifying cation selected from hydrogen and metals of Groups I to VIII of the Periodic Table or with a compound of at least one Group I to VIII metal.

15 Claims, No Drawings

PROCESS FOR THE PRODUCTION OF HYDROCARBONS FROM HETERO-SUBSTITUTED METHANES

The present invention relates to a process for the production of hydrocarbons from hetero-substitued methanes.

The forecast longer-term shortage of petroleum has in recent years stimulated research into the production of chemicals and fuels from other raw materials. In particular both coal and natural gas, of which there are vast reserves, have been under consideration because both are readily converted by well established technology into a mixture of gases comprising carbon monoxide and hydrogen, conventionally referred to as synthesis gas, which in turn can be converted into methanol. Methanol is a useful intermediate for the production of valuable chemicals, for example acetic acid, ethanol, esters, acetic anhydride etc and in recent years its use has been proposed both as a gasoline blending component and as a feedstock for the production of liquid gasoline range hydrocarbons by conversion over synthetic crystalline aluminosilicate catalysts, see for example U.S. Pat. No. 4,138,442 (Mobil).

In U.S. Pat. No. 3,894,107 (Mobil) there is described a process for converting an aliphatic organic compound of the formula R-X where X is at least one of halogen, oxygen, sulphur or nitrogen to a product comprising a complex mixture of compounds. The product including hydrocarbon compounds having a greater number of carbon atoms than the organic compound reactant, a higher ratio of carbon atoms to heteroatoms than the organic compound reactant and a longest carbon to carbon chain length which is longer than the longest carbon chain length of the organic compound reactant. The process is carried out by contacting the compound of formula R-X with a crystalline aluminosilicate zeolite having a silica to alumina ratio of at least about 12 and a constraint index of about 1 to 12. It is further stated that the zeolite may be in the hydrogen form or it may be base exchanged or impregnated to contain ammonium or a metal cation complement, of which the latter may be a cation of the metals of the Groups I through VIII of the Periodic Table. No specific cation-exchanged form of the zeolite is identified as being desirable for the conversion of any of the reactants embraced by the formula R-X, nor indeed is any specific cation-exchanged form of the zeolite said to be desirable for the conversion of compounds of the formula R-X as a generic class. The Examples illustrate only the use as catalyst of an aluminosilicate zeolite in the hydrogen form and 24 of the 26 Examples are devoted to alkanol conversions, the remaining two being directed to methyl mercaptan conversion and tri-n-butylamine conversion. Of the Examples on alkanol conversion, the majority are devoted to the use of methanol as the feedstock.

U.S. Pat. No. 3,894,104 describes a process for converting a feed comprising compounds of the type $(R)_n$-X where R is a lower hydrocarbon moiety having 1 carbon atom, X is a hetero moiety selected from the group consisting of oxygen, hydroxyl, sulphur, nitrogen, halogen and cyanide and n is a number up to the valence of X, to other compounds having a higher ratio of R to X than in the feed by contacting such feed with a crystalline aluminosilicate zeolite catalyst, having a silica to alumina ratio of at least about 12 and a constraint index of about 1 to 12, at an elevated temperature of about 500° to about 750° F. at a space velocity of about 0.1 to 50 LHSV; the improvement, comprises utilising as the catalyst the zeolite which has been modified by the incorporation therewith of at least one metal of Group Ib, IIa, IIb, IIIa, IVa and VIII of the Periodic Table. Representative feeds are said (column 5, lines 33 to 38) to include alcohols, particularly methanol, ethers, particularly dimethyl ether, ketones, particularly acetone and analogous and homologous materials such as mercaptans or amines, in admixture with each other and/or in admixture with other materials. The specific metals are incorporated in the catalyst for the purpose of increasing the aromatics content of the product. All 25 Examples are directed to the conversion of methanol.

An alternative approach to the conversion of methane, which forms the principal component of natural gas, to hydrocarbons in the gasoline boiling range is to convert the methane to a monohalomethane and thereafter to catalytically convert same to hydrocarbons. This route is potentially more attractive than the methanol route because it eliminates one step in the process in that methane is converted directly at high selectivities to monohalomethane. Moreover, the hydrogen halide produced as a by-product during conversion to monohalomethane can be recycled to the monohalomethane production process, whereas the by-product of the methanol conversion process is not so utilisable. The chemistry of the conversion of methanol, and alcohols in general, as compared with monohalomethanes differs considerably; for example at low temperatures methanol is converted to dimethyl ether whereas the analogous reaction is not possible for monohalomethanes. Another significant difference is that in the case of methanol conversion water is co-produced, whereas the conversion of monohalomethanes co-produces hydrogen halides which are known to dealuminate crystalline aluminosilicate zeolite structures leading to framework collapse and irreversible loss in catalytic activity. Dealumination would be anticipated to be more serious in the presence of hydrogen halides than in the presence of water. Conclusions drawn from the prior art regarding methanol conversion are therefore not necessarily applicable to monohalomethane conversions.

Japanese patent publication No. J55073-619 teaches that methane can be converted into methyl chloride and thereafter dehydrochlorinated using a zeolite to produce hydrocarbons having at least 2 carbon atoms. The zeolite employed is a silicate mineral consisting of $SiO_2$, $Al_2O_3$ and an alkali metal or an alkaline earth metal.

We have now found that monohalomethanes can be efficiently converted to higher aliphatic hydrocarbons and hydrocarbons in the gasoline boiling range. Within a certain temperature range, the selectivity to desirable aliphatic hydrocarbons can be high using cation-exchanged synthetic crystalline gallosilicate catalysts. The term 'gallosilicate' as used herein is intended to embrace both a crystalline silica in which the whole of the gallium is present in the crystal lattice of the silica in place of its silicon atoms and also a crystalline silica in which part of the gallium is present as aforesaid and the remainder is present in other locations, for example in the pores thereof and/or on the surface of the crystalline silica. The activity of the catalysts can be maintained for substantial periods and some at least of the catalysts can be regenerated.

Accordingly, the present invention provides a process for the conversion of a monohalomethane to a product comprising hydrocarbons having at least 2 carbon atoms which process comprises contacting the monohalomethane at elevated temperature with a synthetic crystalline gallosilicate loaded either with at least one modifying cation selected from hydrogen and metals of Groups I–VIII of the Periodic Table or with a compound of a least one Group I–VIII metal.

As regards the monohalomethane, the halo-moiety may suitably be fluoro-, chloro- or bromo-, preferably chloro-. The monohalomethane may be used in substantially pure form or may be admixed with its polyhalogenated analogues or with diluents inert under the reaction conditions, e.g. nitrogen, or with hydrogen, oxygen, air, carbon oxides or hydrocarbons. As regards mixtures of polyhalogenated methanes and monohalomethanes, the amount of the polyhalogenated methane which can be tolerated in the mixture will depend upon the degree of halo-substitution, the nature of the gallosilicate and the nature of the cation. Monohalomethanes may suitably be obtained by halogenation or oxyhalogenation of methane or may be derived from methane in admixture with ethane and/or propane in the form, for example, of natural gas. Suitable processes for selectively producing monohalomethanes are described in our copending UK application publication No. 2120249 (BP Case No. 5350) and our copending European application publication No. 0117731 (BP Case No. 5538), and for the selective production of the monochlorides or bromides of $C_1$ to $C_4$ paraffinic hydrocarbons in our UK application No. 8325603 (BP Case No. 5648), the subject matter of which is incorporated by references herein.

Synthetic crystalline silicas modified by incorporation of gallium are known from U.S. Pat. No. 3,702,886; GB-A-2,024,790 and GB-A-2023562, for example.

U.S. Pat. No. 3,702,886 describes a ZSM-5 composition identified, in terms of mole ratios of oxides, as follows:

$$0.9\pm0.2M_{2/n}O:W_2O_3:5-100YO_2:zH_2O$$

wherein M is a cation, n is the valence of said cation, W is inter alia gallium, Y is inter alia silicon and z is from 0 to 40. A method for the preparation of the composition is also described.

GB-A-2024790 describes a silica-based material comprising crystalline silica which has been modified with one or more elements present in the crystal lattice of the silica in place of silicon atoms or is present in the form of salts of bisilicic or polysilicic acids.

GB-A-2023562 describes a gallium-modified silica having a porous crystalline structure and a specific surface area greater than 150 m²/g and having the general formula (P):

Si.(0.0012 to 0.0050)Ga.O$_y$     (P)

wherein y is from 2.0018 to 2.0075. The gallium-modified silicas are prepared by reacting a derivative of silicon and a derivative of gallium with a template, the reaction being carried out in an aqueous medium, an alcoholic medium or an aqueous alcoholic medium; crystallising the reaction mixture at a temperature of from 100° to 220° C.; cooling the reaction mixture; and heating the precipitate in air at a temperature of from 300° to 700° C. The substance which has a templating action is preferably a tertiary amine, an amino alcohol, an amino acid, a polyhydric alcohol or a quaternary ammonium base such as a tetraalkylammonium base (e.g. NR$_4$OH wherein R is an alkyl radical having from 1 to 5 carbon atoms) or a tetraarylammonium base (e.g. NR'$_4$OH wherein R' is a phenyl or an alkylphenyl radical). In a modification of the invention of GB-A-2023562 an MFI zeolite has the general compositional formula as follows (Q):

$$(0.9\pm0.2)M_{2/n}O:W_2O_3:(5-100(YO_2:zH_2O \qquad (Q)$$

wherein M is a cation selected from H$^+$ and/or NH$_4^+$ and/or metallic cations and/or cations deriving from amino alcohols (especially ethanolamines), n is the valency of the cation, W is gallium, Y is silicon and z is from 0 to 40. A method for preparing a zeolite of the formula (Q) is described.

The aforesaid gallosilicates prepared in the manner described, are examples of synthetic crystalline silicas which may be used after modification in the process of the invention. It is preferred to use a gallosilicate having an MFI structure and having the general formula (Q) as described hereinbefore.

Before use in the process of the invention, the gallosilicate is loaded with either the modifying cations or a compound thereof. In the case of loading with the modifying cations the templating cations in the as-prepared gallosilicate are replaced at least in part with the modifying cations, i.e. at least one cation selected from hydrogen ions, or ions of a metal of Groups I–VIII of the Periodic Table. Suitable examples of ions are those of sodium, cerium, copper, magnesium, lanthanum, nickel, titanium, iron, zinc, aluminium, gallium and tin. It is preferred to ion-exchange substantially all the templating cations with the modifying cations. Cation-exchange may be accomplished by techniques well known in the art and may be effected either at room temperature or at elevated temperature, for example under reflux conditions.

Alternatively, or in addition, the gallosilicates may be loaded with a compound of at least one of the metals of Group I to Group VIII of the Periodic Table. Compounds of the aforesaid metals may be loaded by deposition, suitably by impregnation or precipitation or by any other technique on the crystalline gallosilicate. Deposition is preferably effected by impregnation with a solution of a suitable compound, for example a metal salt, which almost inevitably is accompanied by ion-exchange of exchangeable cations with other cations. The amount of metal or metals loaded whether by deposition of cation exchange may suitably be up to 25% w/w, preferably from 0.1 to 15% w/w calculated as metal(s) and based on the total weight of the catalyst.

Furthermore, the gallosilicate is preferably calcined at least once, suitably before or after loading of the gallosilicate by the modifying cations or a compound thereof. Calcination may suitably be accomplished by heating the crystalline gallosilicate, suitably in a stream of air, oxygen, inert gas, hydrogen or any combination thereof, at a temperature in the range from 200° to 600° C., or above, suitably for at least 0.5 h. At lower temperatures, below 500° C., it may be preferred to calcine at least for 3 hours, preferably 16 hours while at higher temperatures shorter periods may be desired.

The gallosilicate may also be steam treated, suitably before or after calcination and/or before or after cation exchange/deposition. However, if the calcination is carried out prior to steam treatment a further calcination may be necessary to drive off any water present after steam treatment.

The process for the conversion of monohalomethane to hydrocarbons may suitably be effected at an elevated temperature in the range from 80° to 600° C. The pressure may suitably be atmospheric pressure, though higher and lower pressures may be employed if desired.

The process may be operated batchwise or in a continous manner. The Gas Hourly Space Velocity (GHSV) defined as the volume of reactant gas at STP per volume of catalyst per hour for continuous operation may suitably be in the range from 1 to 10,000 vol/vol/hour. The process of the invention can produce aliphatic hydrocarbons in the $C_2$ to $C_{24}$ range at high selectivities, thus rendering it suitable for use as a fuel or fuel supplement. Moreover, such products are transportable from remote locations, either separate or in admixture with crude oil. The process, may for example, fit into a process scheme whereby methane is fed to a first zone wherein it is either halogenated and/or oxyhalogenated to produce monohalomethane at a selectivity based on methane fed of greater than about 80%, the monohalomethane so-produced is passed as feed to the process of the present invention and thereafter the resulting hydrocarbon product is separated from the co-produced hydrogen halide, the hydrogen halide either being recycled to the oxyhalogenation stage or oxidised and the halogen so-produced recycled to the halogenation. The methane may suitably be in the form of natural gas.

The catalyst in the process of the present invention may be employed in the form of a fixed bed or a fluidised bed.

The process of the invention will now be illustrated by reference to the following Examples.

In the Comparison Tests reference will be made to the hydrogen-form of a crystalline aluminosilicate and to silicalite. As regards the hydrogen form of a crystalline aluminosilicate, this has a silica to alumina molar ratio greater than 12, is in the calcined form and has an X-ray diffraction pattern substantially similar to ZSM-5 zeolite. Silicalite is the name given by Union Carbide in U.S. Pat. No. 4,061,724 to a crystalline silica polymorph having an X-ray diffraction pattern similar to that of a ZSM-5 zeolite. Silicalite does not contain aluminium, other than as chance impurity, or indeed any element other than silicon, nor does it have any ion-exchange capacity, i.e. it has no counter-cations associated with its crystal structure. Furthermore, an amorphous gallosilicate is an essentially amorphous silica in which the metal is uniformly distributed.

Furthermore, in a number of Examples and Comparison Tests the terms "aliphatic content" and "Al/Ar ratio" will be employed. The term "aliphatic content" refers to the minimal molar amount of aliphatic hydrocarbons present in the total $C_4$-$C_{14}$ hydrocarbon fraction. The "Al/Ar ratio" refers to the ratio of selectivities of $C_2^+$ - aliphatic to $C_6^+$ - aromatic hydrocarbons. These are terms defined in a manner such as to give an indication of the nature of the product spectra.

Unless otherwise specified the following details apply to all experiments. The reactor was heated externally by means of an electric furnace and the heated zone was maintained at the temperature specified. The applied Gas Hourly Space Velocity (GSHV) in per hourly units at STP are shown in the relevant Tables. The product stream was analysed by on-line gas chromatography.

The compositions of the product streams, excluding unreacted monohalomethane and hydrogen halide, are shown in the relevant Tables together with a summary of experimental details.

Before use, catalysts underwent a pre-treatment as specified below and recorded in the Tables.

Treatment a

Catalysts were treated in air (80 ml/min) at 500° C. for 3 hours and then allowed to cool (100° C. ) before the feed stream selected was switched on. The reaction system was then heated to the required temperature for the specified experiment.

Treatments b, c, d, e and f

Catalysts were treated in air (100 ml/min) at 350° C. (b), 450° C. (c), 500° C. (d), 550° C. (e) and 650° C. (f) for three hours and then allowed to cool to the required experimental temperature, after which the feed was passed over the catalyst.

Treatment g

As described for Treatment b but with a longer heat treatment (16 hours).

Treatment dr

Catalysts were ion-exchanged during reflux (5 hours) and then pre-treated as under Treatment d, as opposed to metal ion exchange at room temperature (5 hours).

Treatment dsr

As described under Treatment dr but the refluxing conditions were maintained for one hour only.

Treatment std

The catalyst specified was treated with moist nitrogen (500° C., 4 hours), allowed to cool under nitrogen only and then pretreated as described for Treatment d. In Examples 38, 39 and 40 respectively 31, 51 and 69% v/v steam (balance nitrogen) was applied before Treatment d.

Preparation of crystalline silica modified by incorporation of gallium into the silica lattice A zeolite precursor gel was made as follows: 163.3 g Ludox (AS40, 40% $SiO_2$ by weight) was added to 221.52 g tetrapropylammonium hydroxide (TPAOH) (25% w/w/$H_2O$) and stirred for 2 hours. In a separate beaker, 8.7 g NaOH pellets were added to 91.28 g $H_2O$, and to the resulting solution was added 15.06 g Ga($NO_3$)$_3$.5$H_2O$ in $H_2O$ (100 g). The resulting precipitate was stirred for 1 hour, then added to the Ludox/TPAOH, which formed a thick gel. The gel was stirred for a further hour. The ratios of reactants in the gel were:

The gel was put in an autoclave for 72 hours at 170° C. Work up of the white crystalline product gave 64 g of dry (125° C.) product.

The zeolite was converted into the ammonium form as follows:

The above product was calcined at 500° C. (36 hours) in a stream of dry air, to give 57 g dry product. This was ion-exchanged with 1M $NH_4Cl$ (3 exchanges using 4×vol/wt zeolite $NH_4Cl$ solution, each exchange stirred for a minimum of 2 hours at room temperature). Yield of dry (125° C. ) product=55.9 g.

Analysis (X-ray fluoresence and atomic absorption) gave the following results:

21.172 Si:1Ga:0.062Na:0.569 NH$_4^+$

XRD showed the material to be greater than 95% MFI (ZSM-5).

EXAMPLES 1 TO 3

Monochloromethane was fed continously to a reactor containing the hydrogen form of the synthetic crystalline gallosilicate, (MFI-type zeolite, having a silicon to gallium atomic ratio of 27.8). Maintaining the furnace temperature, 327° C., the GHSV was varied from 211, 416 to 771 h$^{-1}$. Experimental details are shown in Table 1.

EXAMPLE 4

Example 1 was repeated with monobromomethane as feed with a GHSV of 284 h$^{-1}$.

EXAMPLES 5 TO 7

The procedure of Examples 1 to 3 was repeated using a similar crystalline gallosilicate with a silicon to gallium atomic ratio of 21.1. Various temperatures and GHSV's were used, as specified in Table 1.

Comparison Tests A to D

The Tests were carried out as described for Examples 1 to 3 using the following catalysts: amorphous gallosilicate (A), gallium impregnated MFI-type silicalite (B) and MFI-type silicalite (C and D). The experimental details are specified in Table 1.

Tests C and D illustrate that under similar conditions, an unmodified MFI-type silicalite is not as active as the catalysts of the present invention. Even when impregnated with gallium alone (Test B) low conversions are obtained with low aliphatic contents and hence a highly aromatic product, in contrast with the high conversions and highly aliphatic products obtained when the claimed hydrogen ion modified crystalline gallosilicate was used.

EXAMPLES 8 TO 10

Mixtures of monochloromethane and 25% v/v methane (Examples 8 and 10) and 50% v/v methane were fed continuously to a reactor, as described for Examples 1 to 3. Details and the product distribution, excluding methane, are shown in Table 1. The calculated conversions are based upon the assumption that all higher hydrocarbons originate from monochloromethane.

EXAMPLES 11 AND 12

Experiments were carried out as described under Examples 1 to 3 except that the hydrogen form of a crystalline MEL-type gallosilicate was used, having a silicon to gallium atomic ratio of 20.0. Details are shown in Table 2.

Comparison Tests E and F

Experiments were repeated as for Examples 1 to 3 with the hydrogen form of MFI-type alumino-and galloaluminosilicates. In Test E a crystalline aluminosilicate was used with Si/Al ratio of 20, while in Test F a crystalline galloaluminosilicate was used with Si/Ga ratio of 28.9 and Si/Al ratio of 16.7.

These tests are not examples according to the invention but illustrate that using the crystalline gallosilicates as claimed a far higher aliphatic gasoline product stream is obtained with far less aromatics, as compared with those obtained from using (gallo)aluminosilicates. This can be clearly seen from the low "aliphatic content" (less than or equal to 65%) with the low "Al/Ar" ratio (less than or equal to 2.5) for the (gallo)aluminosilicates as compared with the gallosilicates claimed (respectively greater than or equal to 86% and ranging from 4.6 to 28.6).

EXAMPLES 13 TO 17

The experiments were carried out as described under Examples 1 to 3 with the hydrogen form of a crystalline MFI-type gallosilicate, Si/Ga ratio of 20. Various heat treatments were applied as described under Treatments b to f indicating the importance of various treatments, influencing the activity of the catalyst and modifying the product spectrum, as can be seen in Table 2. Depending on the catalyst treatment a larger C$_5^+$-aliphatics fraction can be obtained if so desired.

EXAMPLES 18 AND 19

Procedure was carried out as described for Examples 1 to 3, but the pretreatment at 350° C. (Treatment b, 3 hours) for Example 18 was extended for Example 19 (Treatment g, 16 hours) resulting in a more active catalyst, see Table 2.

EXAMPLES 20 AND 21

The catalyst used for 21 hours in Examples 15 and 17 were regenerated according to Treatment d and re-used without a major change in catalyst activity.

EXAMPLES 22 TO 28

For Examples 22, 24 and 26 the metal form of the crystalline gallosilicate was obtained by reflux with solutions of the metal salts and Examples 23, 25, 27 and 28 obtained by treating the gallosilicate with solutions of the metal salts at room temperature (see Table 3).

Examples 24 and 26 gave an increased butene fraction (63% and 48%) of the C$_4$-aliphatic products as compared with Examples 25 and 27 (only 48 and 36% respectively). In the case of the sodium form an increased butene fraction (53%) was obtained with room temperature exchange as compared to reflux conditions (39%).

The difference in the results shown for Examples 27 and 28 is due to a marginally higher amount of copper ions in the catalyst of Example 28.

EXAMPLES 29 TO 38

Various amounts of modifying cations/metal compounds were incorporated into the MFI-type gallosilicates used as specified in Tables 3 and 4.

EXAMPLES 39 TO 41

The hydrogen form of MFI-type gallosilicates was pretreated with increasing amounts of steam (31, 51 and 69% steam in nitrogen) as specified under Treatment std and in Table 4.

TABLE 1

| Mol % Product | 1 | 2 | 3 | 4 | 5 | 6 | 7 | A | B | C | D | 8 | 9 | 10 |
|---|---|---|---|---|---|---|---|---|---|---|---|---|---|---|
| Aliphatics | | | | | | | | | | | | | | |
| $C_1$-$C_2$ | 3 | 1 | 5 | 2 | 23 | 29 | 32 | 44 | 29 | 0 | 100 | 5 | 6 | 4 |
| $C_3$ | 24 | 29 | 42 | 22 | 3 | 28 | 26 | 31 | 8 | 0 | 0 | 28 | 31 | 36 |
| $C_4$ | 20 | 26 | 26 | 9 | 52 | 14 | 10 | 21 | 16 | 0 | 0 | 39 | 36 | 38 |
| $C_5$-$C_{11}$ | 47 | 37 | 24 | 65 | 22 | 23 | 24 | 4 | 11 | 0 | 0 | 24 | 20 | 19 |
| Aromatics $A_6$-$A_{14}$ | 6 | 7 | 3 | 2 | 0 | 6 | 8 | 0 | 36 | 0 | 0 | 4 | 7 | 3 |
| Conversion | 91 | 78 | 66 | 24 | 16 | 76 | 82 | 2 | 24 | 0 | 1 | 75 | 65 | 51 |
| Modifying ion | H | H | H | H | H | H | H | | | | | H | H | H |
| Temperature/°C. | 327 | 327 | 327 | 327 | 227 | 327 | 377 | 327 | 327 | 327 | 427 | 327 | 327 | 327 |
| GHSV/$h^{-1}$ | 211 | 416 | 771 | 284 | 158 | 174 | 292 | 197 | 200 | 100 | 89 | 200 | 200 | 400 |
| Treatment | a | a | a | a | a | a | a | a | a | a | a | a | a | a |
| Aliphatic Content | 92 | 90 | 94 | 97 | 100 | 86 | 81 | 100 | 43 | 0 | 0 | 94 | 89 | 95 |
| Al/Ar ratio | 11.9 | 6.6 | 28.6 | 19.7 | — | 4.6 | 4.3 | — | 0.5 | — | — | 9.7 | 5.3 | 15.9 |

TABLE 2

| Mol % Product | 11 | 12 | E | F | 13 | 14 | 15 | 16 | 17 | 18 | 19 | 20 | 21 |
|---|---|---|---|---|---|---|---|---|---|---|---|---|---|
| Aliphatics | | | | | | | | | | | | | |
| $C_1$-$C_2$ | 9 | 12 | 5 | 7 | 4 | 3 | 2 | 3 | 3 | 7 | 6 | 3 | 3 |
| $C_3$ | 39 | 39 | 58 | 49 | 47 | 40 | 33 | 33 | 26 | 43 | 37 | 27 | 23 |
| $C_4$ | 23 | 18 | 20 | 25 | 40 | 35 | 36 | 35 | 35 | 39 | 32 | 35 | 33 |
| $C_5$-$C_{11}$ | 20 | 27 | 4 | 5 | 9 | 18 | 25 | 26 | 31 | 11 | 23 | 29 | 34 |
| Aromatics $A_6$-$A_{14}$ | 9 | 4 | 13 | 14 | 0 | 4 | 4 | 4 | 5 | 0 | 2 | 6 | 7 |
| Conversion | 49 | 82 | 90 | 62 | 21 | 54 | 80 | 88 | 82 | 26 | 58 | 96 | 94 |
| Modifying ion | H | H | H | H | H | H | H | H | H | H | H | H | H |
| Temperature/°C. | 327 | 377 | 327 | 327 | 327 | 327 | 327 | 327 | 327 | 327 | 327 | 327 | 327 |
| GHSV/$h^{-1}$ | 200 | 200 | 200 | 200 | 200 | 200 | 200 | 200 | 200 | 200 | 200 | 200 | 200 |
| Treatment | a | a | a | a | b | c | d | e | f | b | g | d | d |
| Aliphatic Content | 83 | 92 | 65 | 68 | 100 | 93 | 94 | 94 | 93 | 100 | 96 | 91 | 91 |
| Al/Ar ratio | 4.7 | 10.2 | 2.5 | 2.2 | — | 13.1 | 13.6 | 11.8 | 9.7 | — | 12.3 | 7.9 | 7.8 |

TABLE 3

| Mol % Product | 22 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|
| Aliphatics | | | | | | | | | | | | | | | |
| $C_1$-$C_2$ | 11 | 7 | 10 | 3 | 4 | 4 | 3 | 5 | 10 | 6 | 3 | 3 | 3 | 4 | 3 |
| $C_3$ | 38 | 42 | 49 | 32 | 38 | 29 | 31 | 24 | 40 | 26 | 26 | 28 | 29 | 24 | 30 |
| $C_4$ | 36 | 38 | 19 | 37 | 34 | 34 | 17 | 39 | 33 | 35 | 32 | 29 | 32 | 30 | 34 |
| $C_5$-$C_{11}$ | 15 | 13 | 19 | 26 | 21 | 29 | 44 | 24 | 15 | 27 | 34 | 35 | 31 | 35 | 28 |
| Aromatics $A_6$-$A_{14}$ | 0 | 0 | 3 | 2 | 3 | 4 | 5 | 8 | 2 | 6 | 5 | 5 | 5 | 7 | 5 |
| Conversion | 26 | 21 | 34 | 84 | 66 | 71 | 78 | 83 | 86 | 99 | 100 | 88 | 94 | 100 | 88 |
| Modifying ion | Na | Na | Ce | Ce | Cu | Cu | Cu | Al | Al | Zn | Mg | La | Ti | Fe | Ni |
| Temperature/°C. | 327 | 327 | 327 | 327 | 327 | 327 | 327 | 327 | 371 | 327 | 327 | 327 | 327 | 327 | 327 |
| GHSV/$h^{-1}$ | 200 | 200 | 200 | 200 | 200 | 200 | 200 | 200 | 553 | 200 | 200 | 200 | 200 | 200 | 200 |
| Treatment | dr | d | dr | d | dr | d | d | dsr | dsr | dsr | dsr | dsr | dsr | dsr | dsr |
| Aliphatic Content | 100 | 100 | 93 | 97 | 95 | 96 | 93 | 92 | 96 | 91 | 93 | 93 | 93 | 90 | 95 |
| Al/Ar ratio | — | — | 9.9 | 12.2 | 15.3 | 11.3 | 9.8 | 5.2 | 17.6 | 7.6 | 10.7 | 12.2 | 9.9 | 7.5 | 11.7 |

TABLE 4

| Mol % Product | 37 | 38 | 39 | 40 | 41 |
|---|---|---|---|---|---|
| Aliphatics | | | | | |
| $C_1$-$C_2$ | 11 | 2 | 3 | 2 | 2 |
| $C_3$ | 35 | 21 | 29 | 28 | 24 |
| $C_4$ | 25 | 30 | 32 | 30 | 28 |
| $C_5$-$C_{11}$ | 25 | 46 | 32 | 36 | 41 |
| Aromatics $A_6$-$A_{14}$ | 4 | 1 | 4 | 4 | 5 |
| Conversion | 33 | 87 | 88 | 92 | 87 |
| Modifying ion | Sn | Ga | H | H | H |
| Temperature/°C. | 327 | 327 | 327 | 327 | 327 |
| GHSV/$h^{-1}$ | 200 | 200 | 200 | 200 | 200 |
| Treatment | dsr | dsr | std | std | std |
| Aliphatic Content | 93 | 99 | 94 | 94 | 93 |
| Al/Ar ratio | 9.5 | 43 | 12.9 | 13.2 | 12.1 |

We claim:

1. A process for the conversion of a monohalomethane to a product comprising hydrocarbons having at least 2 carbon atoms which process comprises contacting the monohalomethane with a synthetic crystalline gallosilicate loaded either with at least one modifying cation selected from hydrogen and metals of Groups I to VIII of the Periodic Table, or with a compound of at least one Group I to VIII metal.

2. A process according to claim 1 wherein the monohalomethane is monochloromethane.

3. A process according to claim 1 wherein the synthetic crystalline gallosilicate has an MFI structure.

4. A process according to claim 1 wherein the synthetic crystalline gallosilicate, prior to loading, has the general formula:

$$0.9 \pm 0.2 M_{2/n}O : Ga_2O_3 : (5-100) SiO_2 : zH_2O$$

wherein M is a cation selected from $H^+$ and/or $NH_4^+$ and/or metallic cations and/or cations deriving from amino alcohols, n is the valency of the cation, and z is from 0 to 40.

5. A process according to claim 1 wherein the crystalline gallosilicate is loaded by cation-exchange with at least one cation selected from hydrogen, sodium, cerium, copper, magnesium, lanthanum, nickel, titanium, iron, zinc, aluminium, gallium and tin.

6. A process according to claim 1 wherein the crystalline gallosilicate is loaded by deposition of a compound of at least one of the metals sodium, cerium, copper, magnesium, lanthanum, nickel, titanium, iron, zinc, aluminium, gallium and tin.

7. A process according to claim 1 wherein the crystalline gallosilicate is calcined at least once.

8. A process according to claim 1 wherein the crystalline gallosilicate is steam treated.

9. A process according to claim 1 wherein the monohalomethane is contacted with the synthetic crystalline gallosilicate at a temperature in the range 80° to 600° C.

10. A process for the production of a hydrocarbon having at least 2 carbon atoms from methane which process comprises feeding methane to a first zone wherein it is either halogenated or oxyhalogenated to produce a monohalomethane at a selectivity based on methane fed of greater than 80%, separating the monohalomethane so-produced, contacting the monohalomethane with a synthetic crystalline gallosilicate loaded with a modifying cation or a compound thereof as claimed in claim 1 to convert the monohalomethane to a hydrocarbon product and a hydrogen halide, separating the hydrogen halide from the hydrocarbon product and either recycling the separated hydrogen halide to the oxyhalogenation zone or oxidising the separated hydrogen halide and recycling the halogen so-produced to the halogenation.

11. A process according to claim 1, wherein the product comprises aliphatic hydrocarbons having at least 2 carbon atoms.

12. A process according to claim 1, wherein the product comprises from 0 to 9 mol % of aromatic hydrocarbons, and from 91 to 100 mol % of aliphatic hydrocarbons.

13. A process according to claim 1, wherein said product comprises 100 mol % aliphatic hydrocarbons.

14. A process according to claim 11, wherein the product comprises from 9 to 65 mol % $C_5$ to $C_{11}$ aliphatics.

15. A process according to claim 1, wherein the modifying cation is sodium.

* * * * *